US00PP29389P2

(12) United States Plant Patent
Van Swieten

(10) Patent No.: US PP29,389 P2
(45) Date of Patent: Jun. 12, 2018

(54) ***PHALAENOPSIS* ORCHID PLANT NAMED 'PHALFTEQ'**

(50) Latin Name: ***Phalaenopsis* hybrid**
Varietal Denomination: PHALFTEQ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days. days.

(21) Appl. No.: 15/530,593

(22) Filed: Feb. 3, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFTEQ', particularly characterized by having white flowers with a purple fleck at the center, fresh green buds, and fading purple flecks on the lip, 1 to 3 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALFTEQ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFTEQ'.

The new *Phalaenopsis* plant is a product of a planned breeding program conducted by the inventor in Bleiswijk, The Netherlands. The objective of this breeding program was to create a new *Phalaenopsis* plant with numerous attractive and unique white flowers with a purple fleck at the center, fresh green buds, and fading purple flecks on the lip, suitable for potted plant production.

The new *Phalaenopsis* plant 'PHALFTEQ' is a result of cross-pollination made by the inventor in January 2008 in Bleiswijk, The Netherlands of the proprietary female, or seed parent, *Phalaenopsis* hybrid '01-5017' (unpatented) with the proprietary male, or pollen parent, *Phalaenopsis* hybrid '20421-01' (unpatented).

The new *Phalaenopsis* was selected by the inventor as a single plant within the progeny of the stated cross-pollination in a controlled greenhouse in Bleiswijk, The Netherlands in January 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFTEQ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFTEQ' as a new and distinct variety of *Phalaenopsis* plant.

1) White flowers with a purple fleck at the center, fresh green buds, and fading purple flecks on the lip;
2) 1 to 3 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in December 2016. Colors in the photographs may differ from the color values cited in the detailed botanical description, which accurately describe the actual colors of the new variety.

DESCRIPTION OF THE NEW VARIETY

Figure 1:
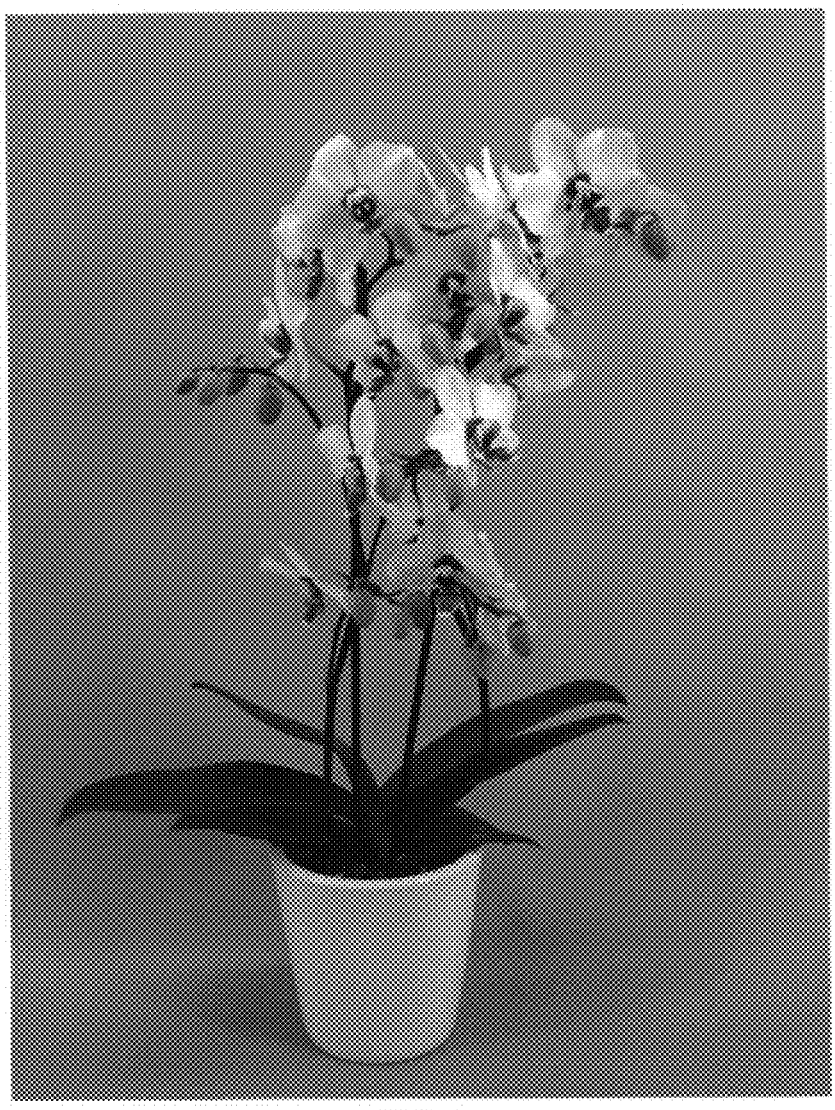
FIG. 1 shows the overall plant habit, including blooms, buds and foliage of 'PHALFTEQ'.
Figure 2:
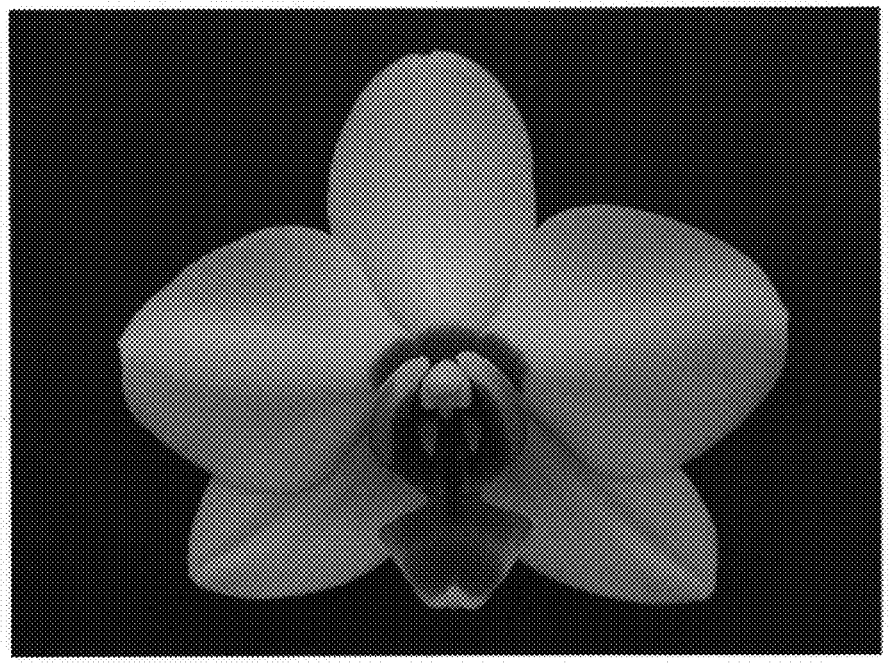
FIG. 2 shows a close-up of a flower of 'PHALFTEQ'.
Figure 3:
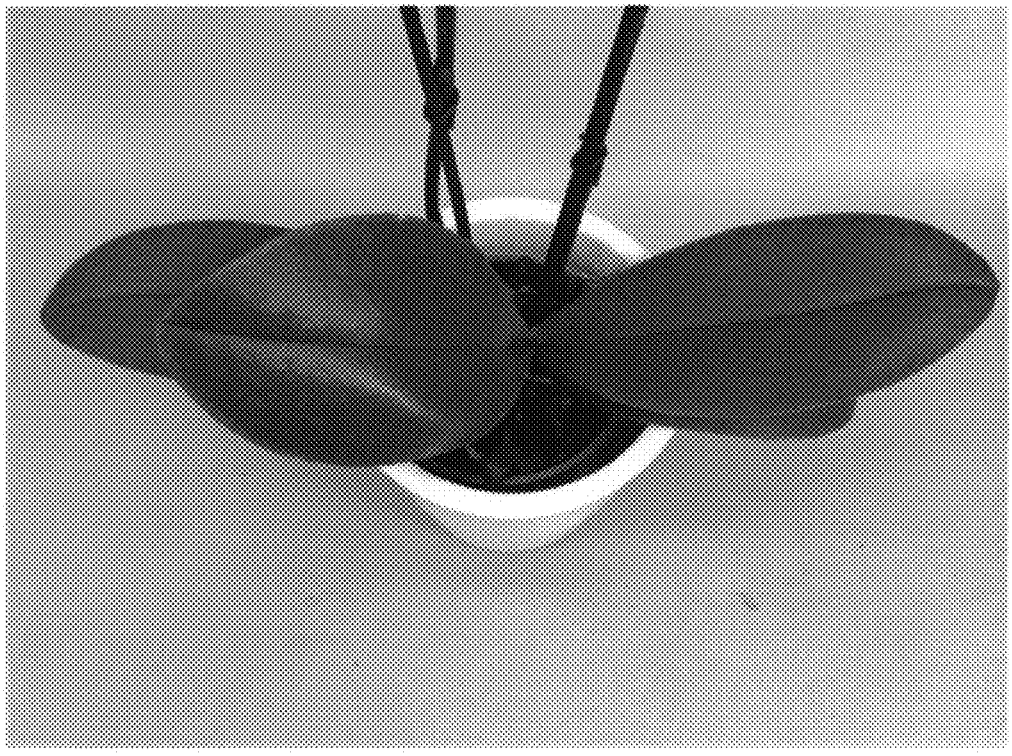
FIG. 3 shows a close-up of the leaves of 'PHALFTEQ'.

The following detailed description sets forth the distinctive characteristics of 'PHALFTEQ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in December 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFTEQ'.

Parentage:

*Female parent*.—*Phalaenopsis* cultivar '01-5017' (unpatented).

*Male parent*.—*Phalaenopsis* cultivar '20421-01' (unpatented).

Propagation:

*Type*.—Meristem tissue culture.

Roots:

*Root description*.—Greyed-green colored roots (RHS 190B/C) with branching lateral roots having light green colored root tips (RHS 145B/C).

Plant:

*Commercial crop time to flowering*.—Approximately 48 to 50 weeks from a rooted cutting to finish in a 12 cm pot.

*Growth habit of peduncle*.—Standard, green leaves, panicle.

*Height (from soil level to top of inflorescence)*.—Approximately 37.0 cm to 47.0 cm.

*Width (measured from leaf tips)*.—About 30.0 cm to 34.0 cm.

*Vigor*.—Strong.

Leaves:

*Mature leaves*.—Quantity per plant: 5 to 8 leaves are produced before flowering. Length (fully expanded): 15.0 cm to 18.0 cm. Width: 8.0 cm to 9.0 cm. Shape: Oblong. Base shape: Moderately elongated. Apex: Unequal obtuse. Leaf blade angle with the petiole (measured from the horizontal position): Between 5 degrees and 20 degrees. Leaf margin: Entire. Color: Upper surface: RHS 147A. Lower surface: RHS 147B with fading dark red edge (RHS 187A). Texture: Slightly rough. Thickness: 2.4 mm to 2.7 mm. Venation: Pattern: Parallel. Color of the midvein: Upper surface: RHS 147A. Lower surface: RHS 187A.

Peduncle:

*Quantity per plant*.—1 to 3.

*Number of flowers per peduncle*.—14 to 22.

*Length*.—38.0 cm to 43.0 cm.

*Diameter*.—4.2 mm to 4.7 mm.

*Strength*.—Moderate.

*Aspect*.—Upright to slightly pendant.

*Texture*.—Smooth.

*Color*.—Mix of brown (RHS 200A) and green (RHS 147B).

*Internode length*.—50.0 mm to 60.0 mm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 170.0 mm to 220.0 mm.

*Flowering time*.—First flowers can be expected 10 to 11 months after planting in a 12 cm (diameter) pot.

*Flower*.—Height: 70.0 mm to 75.0 mm. Diameter: 80.0 mm to 85.0 mm. Depth of lip: 20.0 mm to 22.0 mm.

*Flower longevity*.—On the plant: 9 to 15 weeks.

*Fragrance*.—Absent.

*Flower bud*.—Average size: Medium to large. Length: 20.0 mm to 22.0 mm. Width: 16.0 mm to 18.0 mm. Shape: Egg shaped. Color: Green (RHS 144C) and dark purple at the base (RHS N79A).

*Petals*.—Arrangement: Open/free. Shape: Semi-circular. Apex: Obtuse asymmetric. Margin: Entire. Length (from base to tip): 35.0 mm to 37.0 mm. Width: 35.0 mm to 37.0 mm. Color (when fully opened): Upper surface: Basic color: White (RHS NN155C). Over color: Purple-red fleck (RHS N79C) at the base. Lower surface: Basic color: White (RHS NN155C). Over color: Fading purple fleck (RHS N79D) at the base.

*Dorsal sepal*.—Shape: Elliptic. Apex: Slightly emarginated. Margin: Entire. Length (from base to tip): 40.0 mm to 42.0 mm. Width: 26.0 mm to 28.0 mm. Color (when fully opened): Upper surface: Basic color: White (RHS NN155C). Over color: Small purple-red fleck (RHS N79D) at the base. Lower surface: Basic color: White (RHS NN155C). Over color: Small purple-red fleck at the base (RHS N79D).

*Lateral sepals*.—Shape: Ovate. Apex: Obtuse asymmetric. Margin: Entire. Length (from base to tip): 41.0 mm to 43.0 mm. Width: 23.0 mm to 25.0 mm. Color (when fully opened): Upper surface: Basic color: White (RHS NN155C). Over color: Light green (RHS 145C/D) and purple-red fleck at the base and a few dots (RHS N79C). Lower surface: Basic color: White (RHS NN155C). Over color: Light green (RHS 145C/D) and purple-red at the base (RHS N79C).

*Labellum (lip)*.—Whiskers: Present. Length of whiskers: 4.0 mm to 6.0 mm. Color of whiskers: White. Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 16.0 mm to 18.0 mm. Width: 10.0 mm to 12.0 mm. Color: Dark red at the base (RHS 187B/C) with white on one side (RHS NN155C) and purple on the other side (RHS 77B) with reddish edge (RHS 184C).

*Apical lobe*.—Shape: Trullate. Margin: Entire. Length: 19.0 mm to 21.0 mm. Width: 16.0 mm to 18.0 mm. Color: Purple-red/pink (RHS 186B/C) at the base with dark red stripe in the middle (RHS 187A) and purple fleck (RHS 72A); white (RHS NN155C) toward the whiskers.

*Callus*.—Average size: Small. Height: 0.4 cm to 0.5 cm. Length: 0.3 cm to 0.4 cm. Width: 0.3 cm to 0.4 cm. Color: Dark red (RHS 187A).

*Reproductive organs*.—Column: Length: 9.0 mm to 11.0 mm. Diameter: 4.5 mm to 5.0 mm. Color: White (RHS NN155C). Pollinia: Quantity: 2. Diameter: 0.9 mm to 1.1 mm. Color: Orange (RHS 25A). Ovary: Length: 6.0 mm to 8.0 mm. Diameter: 2.1 mm to 2.3 mm. Pedicel: Length: 34.0 mm to 36.0 mm. Diameter: 2.5 mm to 2.7 mm. Color: Light green (RHS 144B/C) and slightly light purple (RHS N78D) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

The female parent plant of 'PHALFTEQ', cultivar '01-5017' (unpatented), is no longer in existence, so a meaningful comparison cannot be made.

The male parent plant of 'PHALFTEQ', cultivar '20421-01' (unpatented), is not available, so a meaningful comparison cannot be made.

'PHALFTEQ' is most similar to the commercial *Phalaenopsis* plants named 'PHALIFSIB' (U.S. Plant Pat. No. 27,459) and 'PHALFUNEL' (unpatented). 'PHALFTEQ' differs from the commercial variety 'PHALIFSIB' in that 'PHALFTEQ' has a center flower pattern and an apical lobe with purple-red/pink at the base, dark-red stripe in the middle and purple fleck with white toward the whiskers, whereas 'PHALIFSIB' has a dotted flower pattern and a white apical lobe with yellow-green toward the callus and brown edge at the base. Additionally, 'PHALFTEQ' has smaller flowers and much shorter whiskers than 'PHALIFSIB'.

'PHALFTEQ' differs from the commercial variety 'PHALFUNEL' in that 'PHALFTEQ' has a center flower pattern and an apical lobe with purple-red/pink at the base, dark-red stripe in the middle and purple fleck with white toward the whiskers, whereas 'PHALFUNEL' has a flecked flower pattern and a white apical lobe with yellow wings and a stripe in the middle. Additionally, 'PHALFTEQ' has smaller flowers and shorter whiskers than 'PHALFUNEL'.

I claim:

1. A new and distinct variety of *Phalaenopsis* plant named 'PHALFTEQ', substantially as described and illustrated herein.

* * * * *